United States Patent
Hublot et al.

(10) Patent No.: US 10,675,266 B2
(45) Date of Patent: Jun. 9, 2020

(54) COMPOUNDS AND METHODS FOR TREATING AUTISM SPECTRUM DISORDERS

(71) Applicant: BIOCODEX, Gentilly (FR)

(72) Inventors: Bernard Hublot, Compiegne (FR); Rene Levy, Seattle, WA (US); Marie-Emmanuelle Le Guern, Compiegne (FR)

(73) Assignee: BIOCODEX, Gentilly (FR)

( * ) Notice: Subject to any disclaimer, the term of this patent is extended or adjusted under 35 U.S.C. 154(b) by 0 days.

(21) Appl. No.: 16/042,475

(22) Filed: Jul. 23, 2018

(65) Prior Publication Data

US 2018/0325864 A1 Nov. 15, 2018

Related U.S. Application Data

(63) Continuation of application No. 12/634,249, filed on Dec. 9, 2009, now abandoned.

(60) Provisional application No. 61/120,935, filed on Dec. 9, 2008.

(30) Foreign Application Priority Data

Dec. 9, 2008 (EP) ................................ 08305904

(51) Int. Cl.
*A61K 31/36* (2006.01)
*C07D 317/54* (2006.01)

(52) U.S. Cl.
CPC ............ *A61K 31/36* (2013.01); *C07D 317/54* (2013.01)

(58) Field of Classification Search
CPC .............................. A61K 31/36; C07D 317/54
See application file for complete search history.

(56) References Cited

U.S. PATENT DOCUMENTS

| 5,095,033 A | 3/1992 | Levy et al. |
| 7,456,224 B2 | 11/2008 | Chez |
| 2006/0079582 A1 | 4/2006 | Jonas et al. |
| 2010/0029770 A1 | 2/2010 | Roberts et al. |

FOREIGN PATENT DOCUMENTS

| WO | WO 2008/066750 A1 | 6/2008 |
| WO | WO 2008/148023 A2 | 12/2008 |

OTHER PUBLICATIONS

Hollander et al., Nature, Neuropsychopharmacology, 2005, 30, 582-589 (Year: 2005).*
Fisher Janet L: "The anti-convulsant stripentol acts directly on the GABA(A) receptor as a positive allosterid modulator," Neuropharmacology Jan. 2009, vol. 56, No. 1, (Jun. 2008), pp. 190-197.
Belmonte, Pinpointing Austism: Neurochemical Targets and Research Directions in Development Neurobiology, 2002.
Czuczwar S et al: "Stripentol—Characteristic of a new antiepileptic drug," Expert Opinion on Drug Discovery Apr. 2008 GB, vol. 3, No. 4 (Apr. 2008), pp. 453-460.
Dawson, "Early behavioral intervention, brain plasticity, and the prevention of autism spectrum disorder." Development and Psychopathology, 20 (2008), 775-803.
European Examination Report for priority application EP 08 30 5904, dated Jan. 21, 2010.
European Search Report for priority application EP 08 30 5904, dated Jan. 21, 2010.
European Search Report, for EP09178524.6, dated Jan. 21, 2010.
Poisson et al., "A new type of anticonvulsant, Stripentol," Arzneim.-Forsch/Drug Res. 34, No. 2, (1984), pp. 199-204.
Quilichini Pascale P et al: "Stripentol, a putative antiepileptic drug, enhances the duration of opening of GABA—A receptor channels." EPILEPSIA APR 2006, vol. 47, No. 4, (Apr. 2006), pp. 704-716.
Sinkkonen S.T. et al., "Mouse models of Angelman syndrome, a neurodevelopment disorder, display different brain regional GABAA receptor alterations" Neuroscience Letters 340 (2003), pp. 205-208.
Weiss H.R. et al., "Cerebal O2 consuption in young Eker rets, effects of GABA blockade: implication for autism," Int. J. Devl Neuroscience 26, (2008), pp. 517-521.

* cited by examiner

*Primary Examiner* — Umamaheswari Ramachandran
(74) *Attorney, Agent, or Firm* — Arent Fox LLP

(57) ABSTRACT

The present invention relates to a compound of the following formula (I):

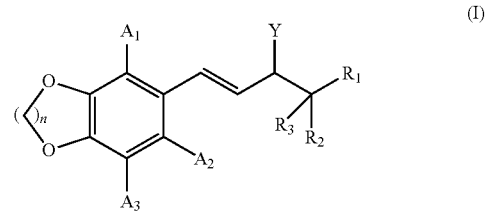

or a pharmaceutically acceptable salt thereof,
for use in the prevention or treatment of autism spectrum disorders (ASD).

6 Claims, 1 Drawing Sheet

COMPOUNDS AND METHODS FOR TREATING AUTISM SPECTRUM DISORDERS

CROSS REFERENCE TO RELATED APPLICATIONS

This application is a continuation of U.S. application Ser. No. 12/634,249 filed Dec. 9, 2009, which claims the benefit of U.S. provisional application 61/120,935 filed on Dec. 9, 2008, and claims priority to EP Patent Application No. 08305904.8 filed Dec. 9, 2008, the disclosures of each of which is incorporated herein by reference.

FIELD OF THE INVENTION

The present invention relates to compounds and methods useful for preventing and treating autism spectrum disorders (ASD).

BACKGROUND OF THE INVENTION

Autism is a cognitive disorder associated with three diagnostic characteristics: abnormal social interaction, impaired communication and repetitive patterns of behavior (Geshwind D H and Levitt P, Curr. Opin. Neurobiol. 17:103, 2007). Autism is part of a spectrum of disorders called autism spectrum disorders (ASD). Autism has an incidence of approximately 1 in 1,000 individuals while ASD has a higher incidence of 1 to 6 per 1000 individuals. Onset is typically prior to three years of age.

There is a consensus that autism is a neurobiological disorder (Luke Y and Tsai M D, Psychosomatic Medicine 61:651, 1999; Levy & Schultz, Lancet 374:1627, 2009). However, no specific neurological or biological marker has been uncovered as the cause of autism and the etiology of autism remains unknown. To date, there is no etiology-based treatment for autism or ASD. The recommended medical intervention is behavioral rather than pharmacological. Physicians and parents of patients with autism focus on approaches such as behavioral modification, training in social skills and speech therapy.

A number of psychopharmacological agents are utilized in children with autism, but only to address specific psychiatric or behavioral symptoms. These agents include: serotonine-related drugs (buspirone, clomipramine, fenfluramine, fluoxetine, fluvoxamine, sertraline), dopamine-related agents (haloperidol, L-dopa, pimozide), epinephrine and norepinephrine-related compounds (beta-blockers, clonidine, desipramine), and a variety of other agents such as opiate antagonists, ACTH, clozapine, risperidone, vitamins B6 and B12 and melatonin.

Thus, while children with ASD are prescribed a number of drugs, there is still no accepted rational therapeutic paradigm designed to address autism or its causes.

Stiripentol (Diacomit, 1-penten-3-ol, 1-(1,3-benzodioxol)-4,4-dimethyl or 4-dimethyl-1-[3,4-methylenedioxy-3,4)-phenyl]-1-penten-3-ol) is a racemic allylic alcohol that is structurally unrelated to other antiepileptic drugs.

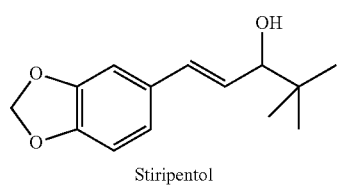 [SMILES: CC(C)(C)C(O)/C=C/c1ccc2c(c1)OCO2]

Stiripentol

Stiripentol has shown anticonvulsant activity in several animal models but its spectrum of clinical activity is relatively narrow. Stiripentol has exhibited a high response rate in SMEI patients at a dose of 50 mg/kg/day. Recently, stiripentol has shown high efficacy in two double blind controlled clinical trials and has received approval from the European Medicines Agency (Chiron C. Lancet 356:1638, 2000).

SUMMARY OF THE INVENTION

The present invention arises from the unexpected observation that resolution of autism symptoms occurs in patients after initiation of treatment with stiripentol. This observation can be confirmed by studies in animal models that mimic characteristic features of autism such as the models described by Moy S S et al, Behav. Brain Res. 176:4, 2007 and McFarlane H G et al, Genes, Brain and Behavior, 1601:1, 2007. Thus, in a mouse model of autism (BALB/c mice), the inventors have shown that stiripentol enhanced the sociability of the mice thereby indicating that stiripentol would be useful in the management of autism.

A number of recent studies have provided support for the notion that the GABAergic system represents an important candidate pathway in autism. The concept is that autism results from an imbalance between inhibitory GABAergic and excitatory glutamatergic pathways. According to this approach, there is overstimulation of the brain with an "inability to filter out excess stimuli from environmental and intrinsic sources" (Collins A L et al, Neurogenetics, 7:167, 2006). This theory is supported by several findings such as decreased GABA-A receptors and benzodiazepine binding sites in the hippocampal formation and linkages between autism and mutations in several GABA receptor subunit genes. Between 2002 and 2007 several studies uncovered an association between autism and GABARB3 polymorphisms in different populations (Buxbaum J D et al, Mol. Psychiatry, 7:311, 2002; Kim S A et al, Neuropsychobiology, 54:160, 2006). Additional studies showed associations with GABARA4, GABARA5 and GABARB1 (Collins A L et al, Neurogenetics, 7:167, 2006).

A recent study by Fisher (Neuropharmacology, 2008 Jun. 10 Epub; 56(1):190-7, 2009) found that stiripentol is a positive allosteric modulator of the GABA receptor acting directly to increase the sensitivity of the receptor to GABA. The study examined the effects of stiripentol on the functional properties of recombinant GABA-A receptors. Among the alpha subunit, the alpha 3 subtype showed the greatest potentiation, while the responses of beta 2 and beta3 subtypes were equivalent and more pronounced than beta1. Additional studies showed that stiripentol acts through a unique site distinct from that of other GABAR modulators (barbiturates, neurosteroids, anesthetics).

Without willing to be bound to any particular theory, it is believed that stiripentol can alleviate the consequences of the mutations of the GABA receptor subunits associated to autism.

The present invention thus relates to a compound of the following formula (I):

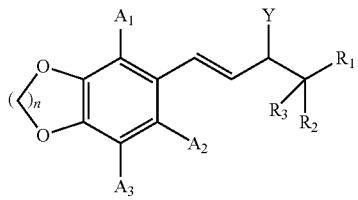

in which:
n represents 1 or 2,
$A_1$, $A_2$ and $A_3$, identical or different, represent a hydrogen atom, a halogen atom, or a linear or branched alkyl group having from 1 to 4 carbon atoms,
$R_1$, $R_2$ and $R_3$, identical or different represent a hydrogen atom or a linear or branched alkyl group having from 1 to 4 carbon atoms, and
Y represents —OH, =O or —SH;
or a pharmaceutically acceptable salt thereof, for use in the prevention or treatment of autism spectrum disorders (ASD).

The present invention also relates to a method for preventing or treating autism spectrum disorders (ASD) in an individual, comprising administering the individual a prophylactically or therapeutically effective amount of the compound of formula (I) as defined above or a pharmaceutically acceptable salt thereof.

In an embodiment of the above-defined compound and method, the compound is combined with at least one additional compound intended for preventing or treating ASD.

The present invention also relates to a pharmaceutical composition comprising as active substances, at least one compound of formula (I) such as defined above, or a pharmaceutically acceptable salt thereof, and at least one additional compound such as defined above, optionally in association with a pharmaceutically acceptable vehicle.

The present invention also relates to products containing:
at least one compound of formula (I) such as defined above, or a pharmaceutically acceptable salt thereof, and
at least one additional compound such as defined above, as a combined preparation for simultaneous, separate or sequential use in the prevention or treatment of ASD.

DETAILED DESCRIPTION OF THE INVENTION

Figure 1:
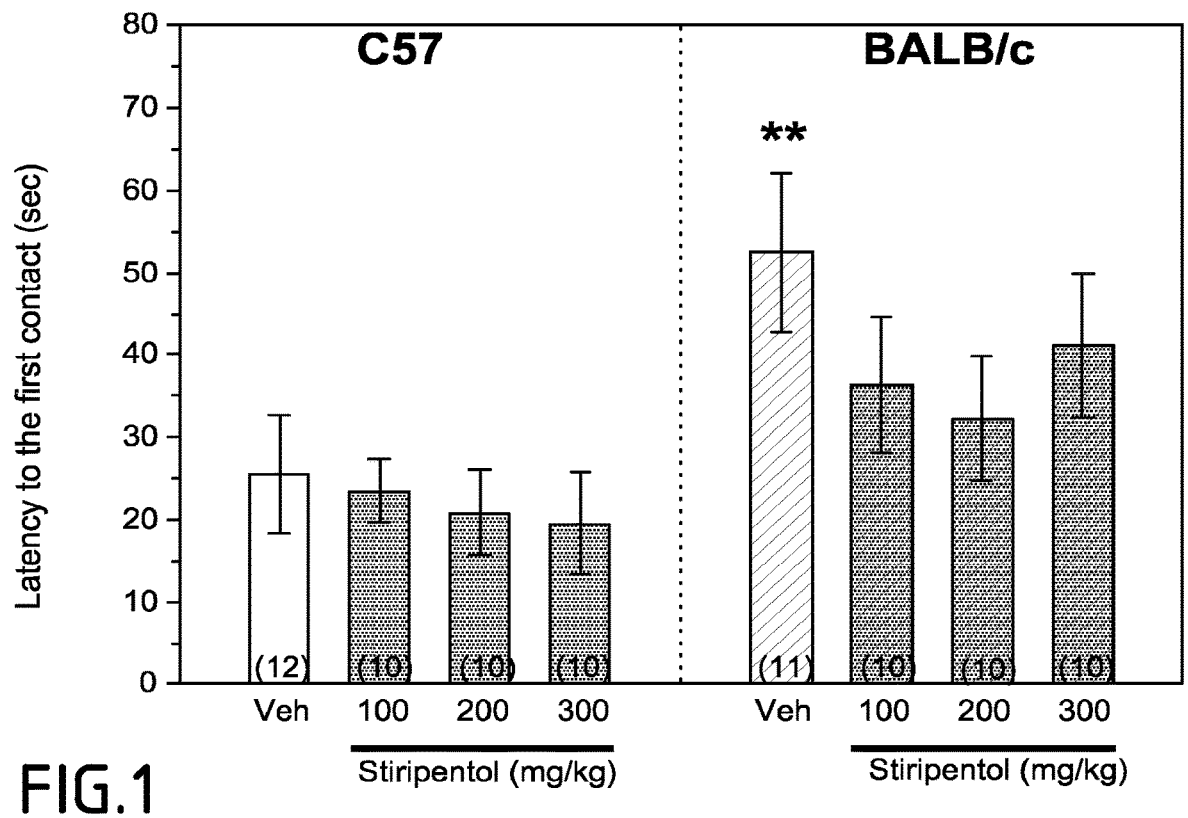
FIG. 1 represents the effect of stiripentol administered by the intra-peritoneal route once daily for 5 days at 0 (vehicle), 100, 200, and 300 mg/kg (horizontal axis) on the latency to the first contact (seconds, vertical axis) of C57 and BALB/c mice. Each bar represents the mean±SEM with the number of animals used at the bottom. **$p<0.01$ compared to vehicle treated C57 mice (two-way ANOVA and Student Newman Keuls test).

Preferably, the above-defined compound of formula (I) is represented by the following formula (II):

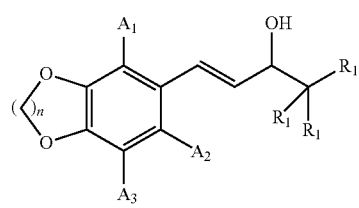

in which n, $A_1$, $A_2$, $A_3$ and $R_1$ are as defined in claim 1.

More preferably the above-defined compound of formula (I) or (II) is represented by the following formula (III):

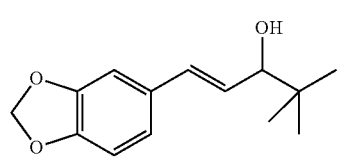

Preferred alkyl groups according to the invention encompass the methyl, ethyl, n-propyl, isopropyl, n-butyl, s-butyl and t-butyl groups. The Cl, I, Br or F atoms are preferred halogen atoms according to the invention.

French patent FR 2 173 691, which is incorporated herein by reference, describes the synthesis of stiripentol, in particular starting from methylenedioxy-3,4-phenyl)-1-dimethyl-4,4-penten-1-on-3. It is well within the ordinary skills of one of skill in the art to synthesize the other compounds of formula (I) from this teaching.

As will be clear to one of skill in the art, the above-defined formulas (I), (II), and (III) represent either the various stereoisomers encompassed by these formulas or mixtures thereof, in particular racemic mixtures thereof.

Thus, the compound of formula (III) can be a compound of formula (IIIa) a compound of formula (IIIb), or a mixture of a compound of formula (IIIa) and a compound of formula (IIIb), in particular the racemic mixture thereof.

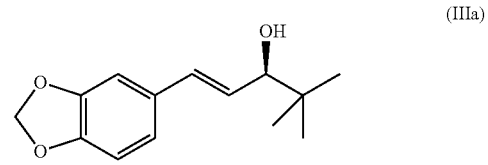 [SMILES: CC(C)(C)C(O)/C=C/c1ccc2c(c1)OCO2]

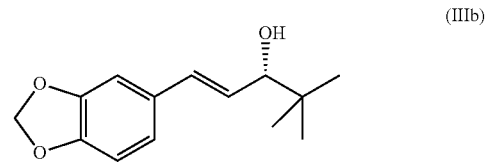

As intended herein the ASD is preferably autism. ASD and autism are notably described in Geshwind D H and Levitt P, Curr. Opin. Neurobiol.17:103, 2007 and in the "Autistic disorder" chapter of the fourth edition of the *Diagnostic and Statistical Manual of Mental Disorders* (DSM-IV) from the American Psychiatric Association, which are incorporated herein by reference.

Preferably also, the ASD is associated to a mutation of at least one GABA receptor subunit.

As intended herein, the expression "a mutation of at least one GABA receptor subunit" indicates that at least one GABA receptor subunit of the individual presents an amino acid which is different from the amino acid which can be found at the same position of the subunit polypeptide in the general population, i.e. in the majority of human beings.

Preferably, the compound of formula (I) as defined above or the pharmaceutically acceptable salt thereof, is to be administered at a unit dose of from 100 mg to 1000 mg. Preferably also, the compound of formula (I) as defined above or the pharmaceutically acceptable salt thereof is to be administered with a dosage regimen of from 10 mg/kg/d to 200 mg/kg/d.

Preferably, the compound of formula (I) as defined above or the pharmaceutically acceptable salt thereof, is in a form suitable for administration by the oral route. Preferably also, the compound of formula (I) as defined above or the pharmaceutically acceptable salt thereof is in the form of sachets, tablets or capsules.

As intended herein, the expression "compound intended for preventing or treating ASD" relates to any compound intended to alleviate one or more of the symptoms of autism spectrum disorders or to treat or prevent autism spectrum disorders.

Preferably, the at least one additional compound intended for preventing or treating ASD as defined above, is selected from the group constituted of serotonine, buspirone, clomipramine, fenfluramine, fluoxetine, fluvoxamine, sertraline, dopamine, haloperidol, L-dopa, pimozide, epinephrine, norepinephrine, beta-blockers, clonidine, desipramine, opiate antagonists, ACTH, clozapine, risperidone, vitamins B6 and B12 and melatonin.

EXAMPLE

The low level of sociability in mice of the BALB/cByJ (hereafter BALB/c) inbred strain is considered to be relevant to autism (Brodkin (2007) *Behav Brain Res* 176:53-65; Moy et al. (2008) *Behav Brain Res* 188:178-194; Brodkin et al. (2004) *Brain Res* 1002:151-157). Furthermore, BALB/c mice show other phenotypes with possible relevance to autism, including relatively high levels of anxiety and aggressive behaviors, large brain size, underdevelopment of the corpus callosum, and low levels of brain serotonin synthesis (Brodkin (2007) *Behav Brain Res* 176:53-65; Moy et al. (2007) *Behav Brain Res* 176:4-20; Sankoorikal et al. (2006) *Biol Psychiatry* 59:415-423; and Moy et al. (2008) *Behav Brain Res* 188:178-194).

The purpose of this study was to examine the effects of stiripentol on the social behavioural in BALB/c mice compared to C57BL/6J (C57) inbred mice. The social investigatory behaviour of mice was measured by the amount of time that the "test" mouse (BALB/c and C57 mice) engaged in social contact with the "stimulus" mouse (juvenile DBA/2J mice strain).

The preliminary results obtained in BALB/C mice were consistent with the data of the literature. They showed that the low level of sociability, previously described in BALB/c, expressed in the present study by less time spent in social contacts toward a different juvenile mouse strain. Such abnormalities characterize autism.

Stiripentol, following a sub-chronic treatment (100, 200 or 300 mg/kg i.p.×5 days), enhanced the sociability in BALB/c mice, leading to an increased duration of social contacts, thereby indicating that stiripentol would be useful in the management of autism.

Materials and Methods

Animals

All male mice (BALB/c, C57 and DBA/2J) were purchased from the Charles River breeding (Les Oncins-France). BALB/c and C57 mice were 8 weeks of age upon arrival at the laboratory. They were housed in temperature-controlled rooms (22±2° C.), separately by strain, with 5 mice per polycarbonate cage (type "S" cage: 265 mm L×160 mm W×140 mm H) and provided with food (A04-SAFE, France) and tap water ad libitum. Behavioral testing was conducted during the light period of a 12-h light:12-h dark cycle (lights on at 7 a.m.). The mice were used for behavioural testing starting 5-7 days after arrival at the laboratory whereas juvenile DBA/2J mice were used at 3-weeks of age and arrived at the laboratory 5 days prior testing. The experiments were conducted in accordance with the European Recommendations (directive 86/609/ECC) for the care and use of laboratory animals.

Behavioral Testing

The general procedure was conducted according to the protocol described by Fishkin and Winslow (1997) *Psychopharmacology* (Berl) 132:335-341 with slight modifications.

Twenty-four hours prior to testing, BALB/c and C57 mice were individually housed in clear cage (type "S" cage). Food and water remained freely available. Individual housing was provided firstly to permit resident male mice an opportunity to scent mark and habituate to their home cage and, secondly to heighten the motivation of "test" mice for social interaction. All the animals were allowed to acclimate to the test room (natural lighting) for at least 1 h prior to testing which was conducted between 9 a.m. and 3 p.m.

The juvenile DBA/2J mouse was placed into BALB/c or C57 mouse cage for a 10-min observation period. The DBA/2J mouse served as "stimulus" mouse for one BALB/c mouse and one C57BL mouse. For each contact, an observer, sitting about 1 m from the cage; recorded the latency to the first contact (or approach) (in sec) towards the "stimulus" mouse and the time (in sec) that the "test" mouse spent in social investigatory behaviour. Nosing, sniffing, pawing, grooming and close following of the "stimulus" mouse by the young adult mouse were considered to be signs of social investigation. Aggressive behaviours, which were essentially absent, such as biting and mounting, were excluded from measurement.

Pharmacological Treatment

Stiripentol (batch 163, Biocodex) was administered by intraperitoneal (i.p.) route at doses of 100, 200 and 300 mg/kg once daily for 5 consecutive days. The last dose was administered 60 min before testing. Control mice received an equal volume (0.1 ml/10 g) of 5% tween 80 (v/v) in saline. The doses of stiripentol used in this experiment were extracted from literature and were devoid of any adverse motor effects (Gasior et al. (1999) *J Pharmacol Exp Ther* 290:1148-1156; Vincent (1991) *Epilepsy Res Suppl* 3:153-156).

Data Analysis

All data represent the mean±standard error of mean (S.E.M.). Treatment effects on mean latency to the first contact and on mean duration of social investigation were analyzed with two-way analysis of variance (ANOVA) with the strain and the treatment as factors. Post-hoc Student-Newman-Keuls test comparisons were performed where indicated by significant interactions between the two factors. For all comparisons, significance was set up at p<0.05 (Sigma Stat, v3.5, SPSS, Chicago, USA).

Results

Latency to the First Contact

As shown in FIG. 1, in the control animals, the latency to the first approach (or contact) of BALB/c mice toward the "stimulus" mouse was significantly higher than this of C57 mice [F (1, 75)=12.069, p<0.001 for the strain factor]. A trend for decrease in the latency to the first contact was observed in BALB/c mice treated with stiripentol. Stiripentol up to 300 mg/kg dose was without effects in C57 mice ([F (3, 75)=1.102, p=0.354 for the treatment factor].

Duration of Social Contacts

Figure 2:
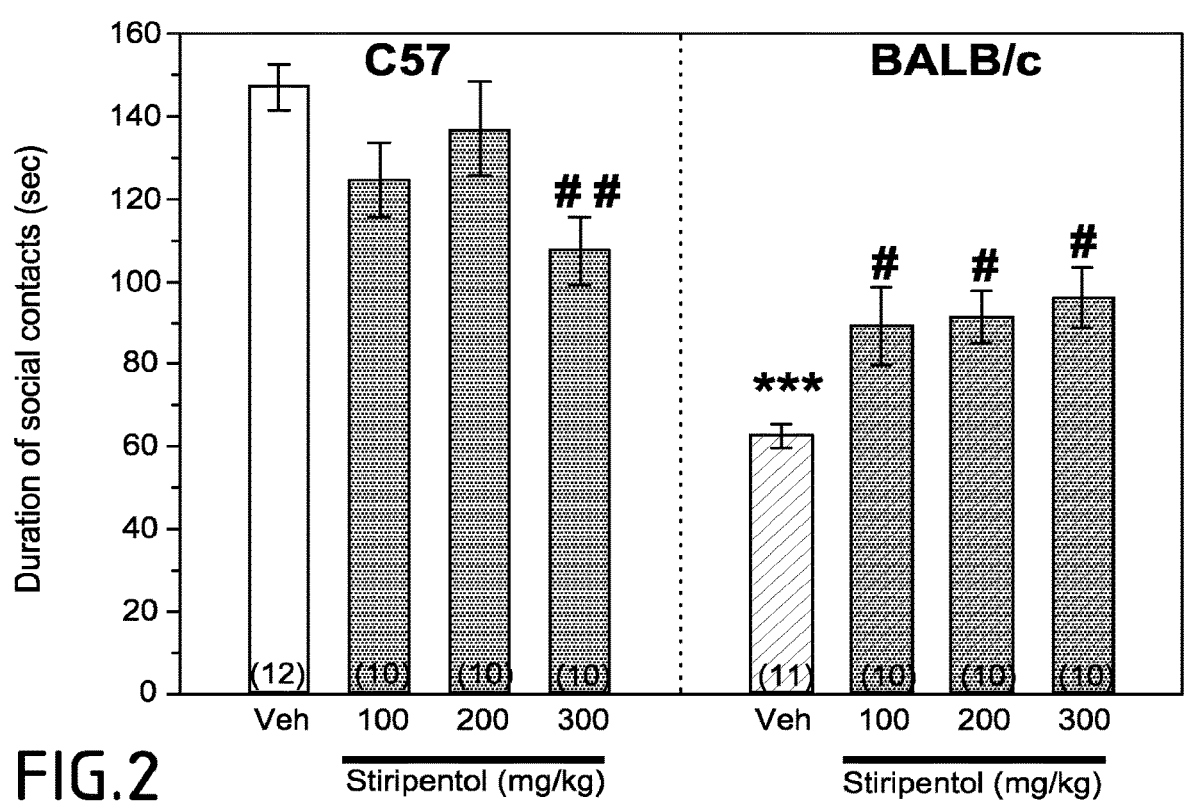
FIG. 2 represents the effect of stiripentol administered by the intra-peritoneal route once daily for 5 days at 0 (vehicle), 100, 200, and 300 mg/kg (horizontal axis) on the duration of social contacts (seconds, vertical axis) of C57 and BALB/c mice. Each bar represents the mean±SEM with the number of animals used at the bottom. ***$p<0.01$ compared to vehicle treated C57 mice. # $p<0.05$, ## $p<0.01$ compared to vehicle treated mice in the same strain (two-way ANOVA and Student Newman Keuls test).

In the control animals, BALB/c mice spent less time in social contacts compared to C57 mice [F (1, 75)=65.792, p<0.001 for the strain factor] (FIG. 2). It is noticed that stiripentol significantly increased the duration of social contacts at the three doses tested in BALB/c mice.

Conversely, this same compound at 300 mg/kg significantly lowered the duration of social contacts in C57 mice [F (3, 75)=8.080, p<0.001, interaction between strain×treatment]. At this dose, sedative effects in C57 mice began to appear and likely underlie the decrease in social contacts duration.

These results indicate that stiripentol would be useful in the treatment of autism.

All the cited references are incorporated herein by reference.

The invention claimed is:

1. A method for the treatment of autism spectrum disorders (ASD) in an individual, comprising administering to the individual a therapeutically active amount of the compound of the following formula:

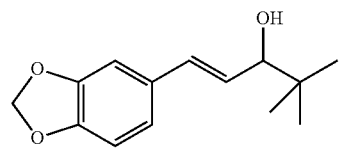 [SMILES: CC(C)(C)C(O)/C=C/c1ccc2c(c1)OCO2]

or a pharmaceutically acceptable salt thereof, wherein the ASD is autism, and wherein the compound or the pharmaceutically acceptable salt thereof is administered with a dosage regimen of from 10 mg/kg/d to 200 mg/kg/d.

2. The method of claim 1, wherein the ASD is associated to a mutation of at least one GABA receptor subunit.

3. The method of claim 1, wherein the compound or the pharmaceutically acceptable salt thereof is administered at a unit dose of from 100 mg to 1000 mg.

4. The method of claim 1, wherein the compound or the pharmaceutically acceptable salt thereof is in a form suitable for administration by the oral route.

5. The method of claim 1, wherein the compound or the pharmaceutically acceptable salt thereof is in the form of sachets, tablets or capsules.

6. The method of claim 1, wherein the compound or the pharmaceutically acceptable salt thereof is administered in combination with at least one additional compound intended for treating ASD selected from the group constituted of serotonin, buspirone, clomipramine, fenfluramine, fluoxetine, fluvoxamine, sertraline, dopamine, haloperidol, L-dopa, pimozide, epinephrine, norepinephrine, clonidine, desipramine, opiate antagonists, ACTH, clozapine, risperidone, vitamins B6 and B12 and melatonin.

* * * * *